(12) United States Patent
Caberg et al.

(10) Patent No.: US 8,409,100 B2
(45) Date of Patent: Apr. 2, 2013

(54) ULTRASOUND TREATMENT HEAD FOR AN APPARATUS FOR TREATING A PATIENT WITH ULTRASOUND

(75) Inventors: Theodorus Johannes Virginia Caberg, Eben-Emael (BE); Ronald Scharp, Den Hoorn (NL); Johannis Van Groningen, Oude Tonge (NL)

(73) Assignee: Enraf-Nonius B.V., Rotterdam (NL)

( * ) Notice: Subject to any disclaimer, the term of this patent is extended or adjusted under 35 U.S.C. 154(b) by 472 days.

(21) Appl. No.: 12/505,595

(22) Filed: Jul. 20, 2009

(65) Prior Publication Data

US 2010/0022889 A1    Jan. 28, 2010

(30) Foreign Application Priority Data

Jul. 23, 2008   (EP) ..................... 08161003

(51) Int. Cl.
*A61B 8/00*   (2006.01)
(52) U.S. Cl. ........................... 600/459; 601/2
(58) Field of Classification Search ............ 600/459; 601/2
See application file for complete search history.

(56) References Cited

U.S. PATENT DOCUMENTS

| | | | | |
|---|---|---|---|---|
| 4,355,643 | A | * | 10/1982 | Laughlin et al. .......... 600/454 |
| 5,579,769 | A | * | 12/1996 | Yoshida et al. .......... 600/437 |
| 5,618,275 | A | | 4/1997 | Bock |
| 5,656,284 | A | * | 8/1997 | Balkin .................... 424/435 |

| | | |
|---|---|---|
| 2003/0171675 A1 | 9/2003 | Rosenberg |
| 2005/0096547 A1 | 5/2005 | Wendelken |
| 2007/0299369 A1 | 12/2007 | Babaev |

FOREIGN PATENT DOCUMENTS

| | | |
|---|---|---|
| EP | 1304966 | 5/2003 |
| KR | 20040094221 | 11/2004 |
| WO | WO2006091093 | 8/2006 |
| WO | WO2008002773 | 1/2008 |

OTHER PUBLICATIONS

An Official Search Report of the European Patent Office in counterpart foreign application No. EP 08161003 filed Jul. 23, 2008.

* cited by examiner

*Primary Examiner* — Jonathan Cwern
(74) *Attorney, Agent, or Firm* — Steven M. Koehler; Westman, Champlin & Kelly, P.A.

(57) ABSTRACT

An ultrasound treatment head for an apparatus for treating a patient with ultrasound comprises at least one active element for converting an electric signal into ultrasound and a vacuum cup having an upper part and a lower part. The active element is mounted in the upper part and the vacuum cup provides a vacuum chamber with a holding space for a gel pad. The upper part is adapted to act as a spring suspension for the active element to lower the active element into the lower part. The active element is provided with a positioning ring protruding with respect to the active element. This positioning ring determines the location of the gel pad within the holding space.

19 Claims, 3 Drawing Sheets

ULTRASOUND TREATMENT HEAD FOR AN APPARATUS FOR TREATING A PATIENT WITH ULTRASOUND

This Application claims priority to European Application No. EP08161003.2, filed Jul. 23, 2008.

BACKGROUND

The discussion below is merely provided for general background information and is not intended to be used as an aid in determining the scope of the claimed subject matter. WO2006/091093 discloses an ultrasound treatment head comprising at least one active element for converting an electric signal into ultrasound, a vacuum cup having an upper part and a lower part, wherein the active element is mounted in the upper part and the vacuum cup provides a vacuum chamber with a holding space for a gel pad. The treatment head can be fixed to the part of the patient's body to be treated in a relatively simple manner by using an underpressure generated in the vacuum cup by a vacuum pump. The vacuum pump can be part of the apparatus for treating a patient with ultrasound. In this manner the person in attendance does not need to stay with the patient during the treatment. The acoustic coupling between the active element and the part of the body that is to be treated depends on the fixation of the treatment head on the body part and the effectiveness of the coupling medium, generally water, provided by the gel pad. To this end the percentage of the coupling medium in the gel pad should be high. However, a high percentage of coupling medium results in a very slippery gel pad surface, so that in the known treatment head it is very difficult if not impossible to keep the gel pad located between the active element and the body part of the patient during a treatment.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

An embodiment of an ultrasound treatment head for an apparatus for treating a patient with ultrasound is described herein The treatment head includes at least one active element for converting an electric signal into ultrasound, a vacuum cup for holding the treatment head on a body part of a patient when an underpressure is generated within the vacuum cup. The vacuum cup has an upper part and a lower part, wherein the active element is mounted in the upper part and the vacuum cup provides a vacuum chamber with a holding space for a gel pad. The upper part is adapted to act as a spring suspension for the active element to lower the active element into the lower part. The upper part moves downwardly when an underpressure is generated within the vacuum cup. The active element is provided with a positioning ring protruding with respect to the active element, said positioning ring determining the location of the gel pad within the holding space.

In this way an ultrasound treatment head is obtained in which the positioning ring provides for a fixed location of the gel pad as desired between the active element and the body part during the complete treatment, wherein the spring suspension of the active element in the upper part causes the active element to be pressed against the body part of the patient to be treated with the gel pad being located between the active element and this body part. The positioning ring guarantees that the gel pad will not be displaced from its desired location by the underpressure generated within the vacuum chamber and/or the force pressing the active element with the gel pad against the body part to be treated.

Furthermore a gel pad is provided for use in combination with the ultrasound treatment head described. The gel pad has a disc shape with a diameter smaller than the inner diameter of the positioning ring and a thickness larger than the protruding length of the positioning ring.

BRIEF DESCRIPTION OF THE DRAWINGS

Aspects of the invention will now be explained in more detail with reference to the drawing, which shows an embodiment of the ultrasound treatment head for an apparatus for treating a patient with ultrasound.

DETAILED DESCRIPTION OF AN ILLUSTRATIVE EMBODIMENT

Figure 1:
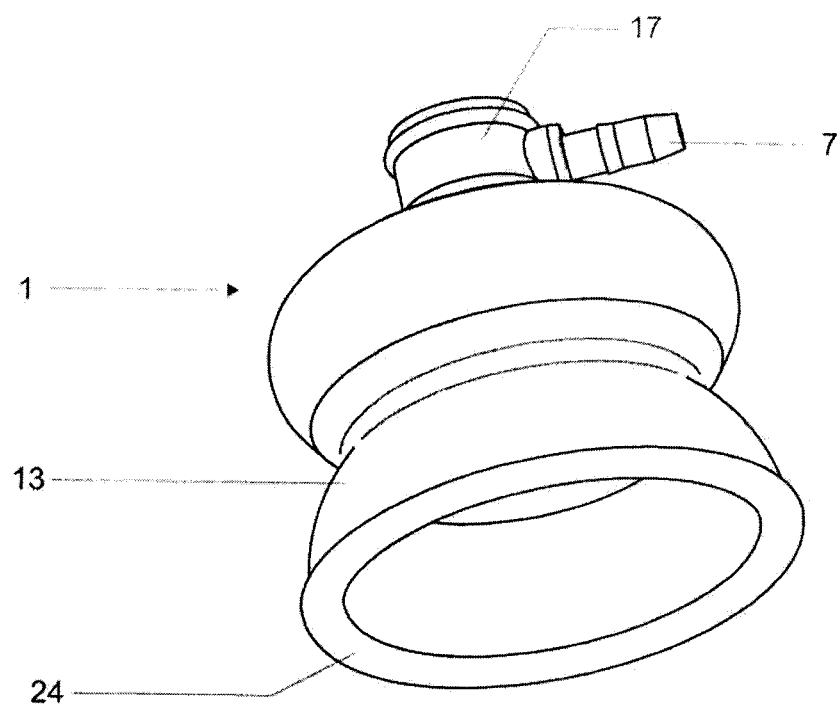
FIG. 1 is a perspective view of an embodiment of the ultrasound treatment head.
Figure 2:
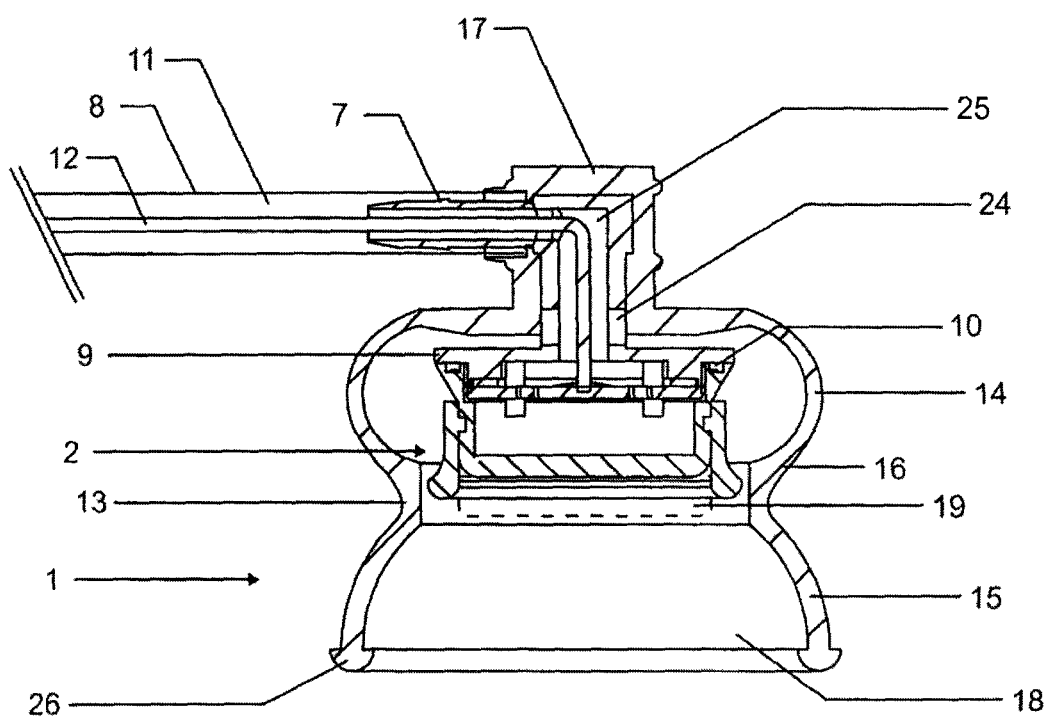
FIG. 2 is a schematic cross-sectional view of the ultrasound treatment head that is shown in FIG. 1.

FIGS. 1 and 2 show an ultrasound treatment head 1 for an apparatus for treating a patient with ultrasound not further shown. An example of a suitable apparatus is shown in WO2006/091093. Such an apparatus is provided with an ultrasound generator known per se, to which the treatment head 1 can be connected. The treatment head 1 is provided with an active element 2 provided with a cylindrical housing 3 with a disc-shaped lower face 4 and a cylindrical outer wall 5. The cylindrical outer wall 5 is connected to a carrier 6 comprising a connecting element 7 for a line 8 only partially shown in FIG. 2, and a mounting disc 9. The cylindrical outer wall 5 is mounted by means of a screwed connection to the mounting disc 9 in the illustrated embodiment, with an O-ring 10 providing a seal.

The line 8 is configured as a combination of a vacuum line 11 and an electric line 12. The electric line 12 is sealingly passed through the mounting disc 9 to the active element 2. The electric line 12 provides the electrical connection between the electronic components, which are known per se, and the ultrasound crystal that forms part of the active element 2. These components are not shown in the drawing.

The treatment head 1 is further provided with a vacuum cup 13 having an upper part 14 and a lower part 15. As shown in FIG. 2 the upper part 14 has a side wall with a semi-circular cross-section and the lower part 15 has a bell shape, i.e. the side wall of the lower part 15 gradually flares outwardly in a mainly circular path in cross-section. The upper and lower parts 14,15 are interconnected through an intermediate stiffening section 16. In the embodiment shown, the parts 14, 15 and section 16 are integrally made formed of a single unitary body of a deformable material, such as silicone rubber.

The side wall thickness of the upper part 14 is less than the side wall thickness of the lower part 15. The carrier 6 with the active element 2 is mounted in the upper wall of the upper part 14, wherein the connecting element 7 of the carrier 6 projects out of a section 17 of the upper wall partially enclosing the carrier 6. In the embodiment shown the upper part 14 is adapted to act as a spring suspension for the active element 2 due to the side wall thickness of the upper part 14 being less than the side wall thickness of the lower part 15. The upper wall with the active element 2 can move downwardly and in this manner the active element 2 can be lowered into the lower part 15 of the vacuum cup 13. This means that the side wall of the upper part 14 folds downwardly when an underpressure is generated within the vacuum cup 13, wherein this side wall acts as a spring.

Figure 3:
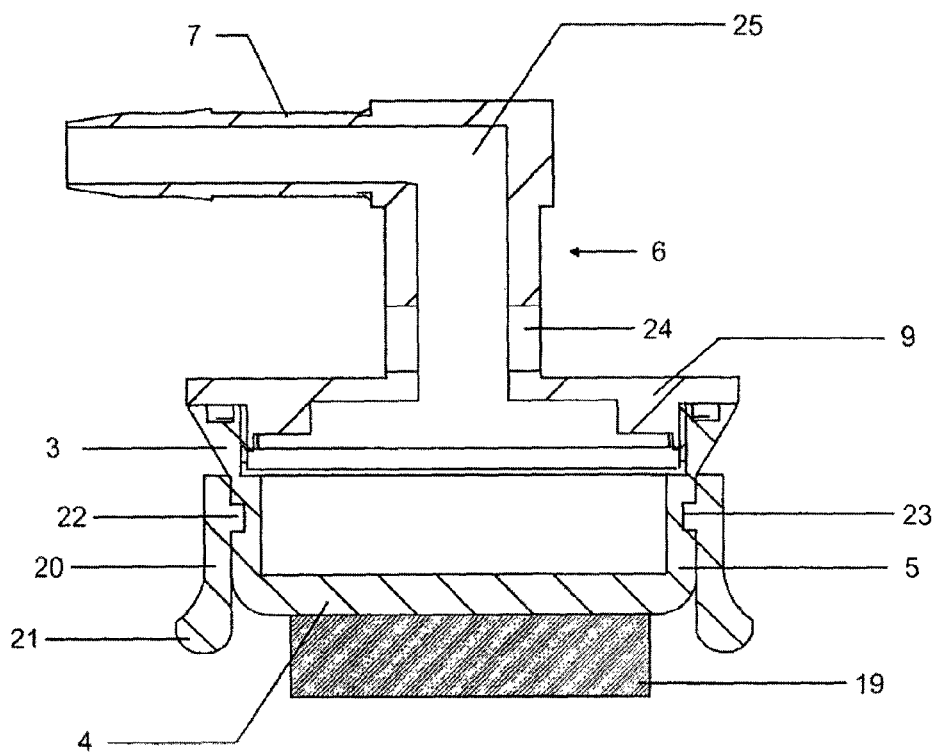
FIG. 3 is a schematic cross-sectional view of the active element of the ultrasound treatment head of FIG. 1 with a gel pad before applying an underpressure to the treatment head.
Figure 4:
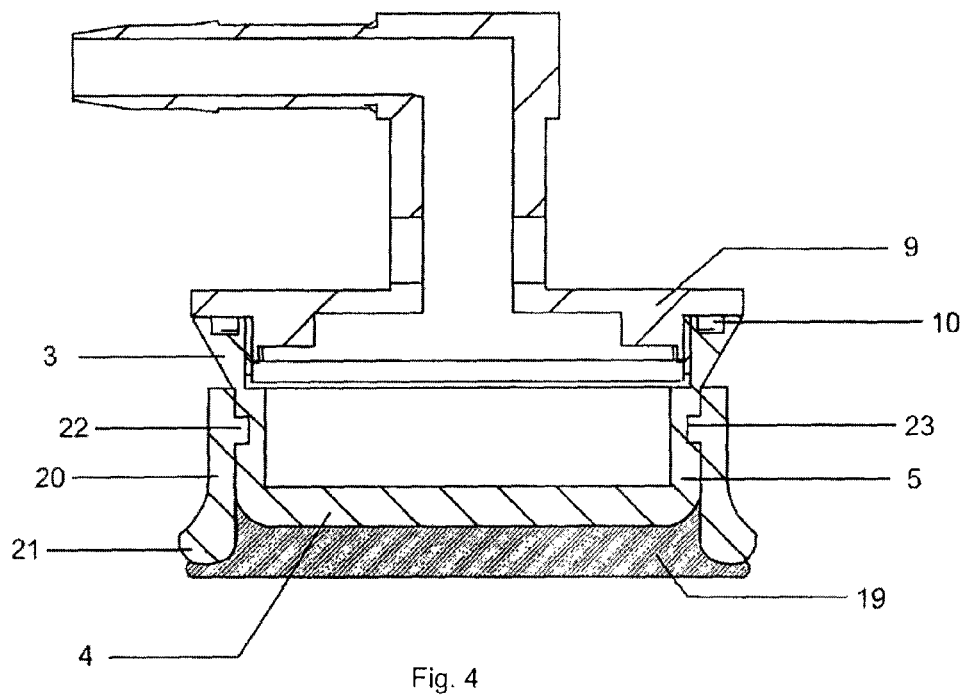
FIG. 4 is a schematic cross-sectional view of the active element of FIG. 3 with a gel pad after applying an underpressure to the treatment head.

The vacuum cup 13 encloses a vacuum chamber 18 with a holding space for a gel pad 19 indicated in FIG. 2 by a dashed line. This gel pad 19 contains a high percentage of water as acoustic coupling medium, so that the surface of the gel pad is very slippery. In order to maintain the gel pad 19 at its desired location in contact with the disc-shaped face 4 of the housing 3 of the active element 2, the active element 2 is provided with a positioning ring 20. This positioning ring can be made of a deformable material, such as silicone rubber. The positioning ring 20 engages the cylindrical wall 5 and protrudes with respect to the disc-shaped face 4 of the housing 4. As shown in FIGS. 3 and 4 at a larger scale the positioning ring 20 is provided with a rounded end edge 21 at its protruding end. In this manner the positioning ring 20 can not damage the gel pad 19 and a gentle contact is obtained between the positioning ring 20 and the skin of the patient.

At its inner side the positioning ring 20 has a ridge 22 engaging into a circumferential recess 23 in the cylindrical wall 5 of the housing 3. This inner ridge 22 received in the recess 23 guarantees a fixed protruding length of the positioning ring 20 during operation of the treatment head.

In FIGS. 3 and 4 the gel pad 19 is shown as located within the positioning ring 20 before and after applying an underpressure in the vacuum cup 13, respectively. As can be seen in FIG. 3 the diameter of the disc-shaped gel pad 19 is smaller than the inner diameter of the positioning ring 20. By way of example the inner diameter of the ring 20 can be 35 mm and the diameter of the gel pad 19 can be 30 mm. More generally, the diameter of the gel pad can be 8-15% smaller than the inner diameter of the positioning ring.

When the treatment head 1 is used a gel pad 19 will be located within the positioning ring 20 against the disc-shaped face 4 of the active element 2 as shown in FIG. 3. The vacuum cup 13 will be placed on the desired location of the body part of the patient to be treated and the vacuum pump of the treatment apparatus (not shown) will generate an underpressure in the vacuum chamber 18 of the vacuum cup 13. The vacuum chamber 18 is connected to the vacuum pump through ports 24 and a channel 25 in the carrier 6 and the vacuum line 11. This underpressure ensures that the treatment head 1 is held in place on the part of the patient's body that is to be treated. Due to the underpressure in the vacuum cup 13 and the spring suspension of the active element 2 in the upper part 14, the active element 2 with the gel pad 19 will move downwards into the lower part 15 of the vacuum cup 13 so that the gel pad 19 is pressed against the skin of the patient. The positioning ring 20 will keep the gel pad 19 at its location between the disc-shaped face of the active element 2 and the patient's skin. The gel pad 19 is slightly deformed as shown in FIG. 4 and provides a good acoustic coupling between the active element 2 and the part of the patient's body on which the vacuum cup 13 is placed. The bell shape of the lower part 15 with its increased thickness prevents a deformation of this lower part 15 at the underpressure values used. The lower part 15 has a rounded end edge 26 to provide a gentle and sealed contact to the skin of the patient.

In the embodiment of the treatment head 1 described, the gel pad 19 comprises a base material containing water as acoustic coupling medium. In one embodiment, the base material of the gel pad 19 is a composition of carrageenan, in particular kappa and iota carrageenan. The gel pad 19 may contain at least 90% water and preferably at least 95% water. With the underpressure used in the treatment apparatus the gel pad 19 will retain its shape as schematically shown in FIG. 4 and the underpressure will not lead to sucking out of the material of the gel pad 19 or the water content or other damage of the gel pad.

It is noted that instead of a treatment head 1 comprising one active element 2 it is also possible to use a treatment head comprising two or more active elements in the apparatus as described herein.

Although the subject matter has been described in a language specific to structural features and/or methodological acts, it is to be understood that the subject matter defined in the appended claims is not necessarily limited to the specific features or acts described above as has been determined by the courts. Rather, the specific features and acts described above are disclosed as example forms of implementing the claims.

What is claimed is:

1. An ultrasound treatment head for an apparatus for treating a patient with ultrasound, comprising:
   at least one ultrasound active element, wherein the active element is provided with a positioning ring protruding with respect to the active element; and
   a vacuum cup configured to hold the treatment head on a body part of a patient, when an underpressure is generated within the vacuum cup, the vacuum cup having an upper part and a lower part, wherein the upper part is semi-circular in cross section and the lower part has a bell shape, gradually flaring outwardly in a mainly circular path in cross-section, the wall thickness of the upper part being less than the wall thickness of the lower part, wherein the active element is mounted in the upper part and the vacuum cup provides a vacuum chamber with a holding space, wherein the upper part is configured to act as a spring suspension for the active element to lower the active element into the lower part, wherein the upper part moves downwardly when an underpressure is generated within the vacuum cup.

2. The ultrasound treatment head according to claim 1, wherein the upper and lower parts of the vacuum cup each comprise a side wall, wherein the side wall of the upper part deflects downwardly, when an underpressure is generated in the vacuum cup.

3. The ultrasound treatment head according to claim 2, wherein the upper part of the vacuum cup joins the lower part through an intermediate stiffening section.

4. The ultrasound treatment head according to claim 1, wherein the active element comprises a cylindrical housing with a disc-shaped lower face, wherein the positioning ring engages the outer wall of the cylindrical housing and protrudes outwardly with respect to the disc-shaped face, the positioning ring having a ridge on its inner side received in a circumferential recess in the outer wall of the cylindrical housing.

5. An ultrasound treatment head according to claim 1, wherein a protruding side of the positioning ring is provided with a rounded end edge.

6. The ultrasound treatment head according to claim 1 and further a gel pad operably coupled to the active element and disposed in the holding space, said positioning ring determining the location of the gel pad within the holding space.

7. The ultrasound treatment head according to claim 6 wherein the gel pad comprises a base material with a coupling medium, wherein the gel pad has a disc shape with a diameter smaller than the inner diameter of the positioning ring and a thickness larger than the protruding length of the positioning ring.

8. The ultrasound treatment head according to claim 7 wherein a base material of the gel pad comprises carrageenan.

9. The ultrasound treatment head according to claim 8 wherein the base material comprises a composition of kappa and iota carrageenan.

10. The ultrasound treatment head according to claim 7 wherein a coupling medium of the gel pad coupling medium is water with a water content of at least 90%.

11. An ultrasound treatment head for an apparatus for treating a patient with ultrasound, comprising:
at least one ultrasound active element, wherein the active element is provided with a positioning ring protruding with respect to the active element; and
a vacuum cup configured to hold the treatment head on a body part of a patient, when an underpressure is generated within the vacuum cup, the vacuum cup having an upper part and a lower part, wherein the active element is mounted in the upper part and the vacuum cup provides a vacuum chamber with a holding space, wherein the upper and lower parts of the vacuum cup each comprise a side wall, wherein the wall thickness of the upper part is less than the wall thickness of the lower part, wherein the upper part of the vacuum cup joins the lower part through an intermediate stiffening section and the side wall of the lower part has a bell shape, gradually flaring outwardly in a mainly circular path in cross-section, wherein the upper part is configured to act as a spring suspension for the active element to lower the active element into the lower part, wherein the upper part deflects and moves downwardly when an underpressure is generated within the vacuum cup.

12. The ultrasound treatment head according to claim 11, wherein the active element comprises a cylindrical housing with a disc-shaped lower face, wherein the positioning ring engages the outer wall of the cylindrical housing and protrudes outwardly with respect to the disc-shaped face, the positioning ring having a ridge on its inner side received in a circumferential recess in the outer wall of the cylindrical housing.

13. An ultrasound treatment head according to claim 11, wherein the positioning ring has a protruding side which protrudes with respect to the active element and which is provided with a rounded end edge.

14. The ultrasound treatment head according to claim 11 and further a gel pad operably coupled to the active element and disposed in the holding space, said positioning ring determining the location of the gel pad within the holding space.

15. The ultrasound treatment head according to claim 14 wherein the gel pad comprises a base material with a coupling medium, wherein the gel pad has a disc shape with a diameter smaller than the inner diameter of the positioning ring and a thickness larger than the protruding length of the positioning ring.

16. The ultrasound treatment head according to claim 15 wherein a base material of the gel pad comprises carrageenan.

17. The ultrasound treatment head according to claim 16 wherein the base material comprises a composition of kappa and iota carrageenan.

18. The ultrasound treatment head according to claim 15 wherein a coupling medium of the gel pad coupling medium is water with a water content of at least 90%.

19. An ultrasound treatment head for an apparatus for treating a patient with ultrasound, comprising:
at least one ultrasound active element, wherein the active element is provided with a positioning ring protruding with respect to the active element; and
a vacuum cup configured to hold the treatment head on a body part of a patient, when an underpressure is generated within a vacuum chamber with a holding space within the vacuum cup, the vacuum cup comprising:
an upper portion wherein the active element is mounted in the upper portion, the upper portion having a first wall thickness;
a middle stiffening portion extending from the upper portion; and
a bottom portion extending from the middle portion, the bottom portion having a second wall thickness that is greater than the first wall thickness, a lower aperture having a first area bounded by a bottom edge, and an upper aperture having a second area opening into the middle portion, the first area being greater than the second area, wherein when an underpressure is generated within the vacuum chamber, the bottom edge of the bottom portion is configured to form a seal with the patient's skin and wherein when a seal is formed with the skin a greater underpressure is generated which causes the upper portion to draw into the vacuum chamber such that the ultrasound active element is positioned proximate the patient's skin, and wherein the upper portion is configured to act as a spring suspension to raise the active element from the bottom portion when there is no underpressure in the vacuum cup.

* * * * *